United States Patent [19]

Hofmann et al.

[11] 4,421,692

[45] Dec. 20, 1983

[54] PROCESS FOR PRODUCING CARBOXYLIC ACID ALKYLESTER AFTER PRODUCTS EXTENSIVELY FREE FROM NITROGENATED COMPOUNDS

[75] Inventors: Peter Hofmann; Wolfgang H. E. Müller, both of Marl, Fed. Rep. of Germany

[73] Assignee: Chemische Werke Hüls AG, Marl, Fed. Rep. of Germany

[21] Appl. No.: 318,661

[22] Filed: Nov. 5, 1981

[30] Foreign Application Priority Data

Dec. 11, 1980 [DE] Fed. Rep. of Germany ....... 3046651

[51] Int. Cl.$^3$ .............................................. C11C 3/02
[52] U.S. Cl. ............................................ 260/410.9 R
[58] Field of Search .................. 260/410.9 C, 410.9 R

[56] References Cited

U.S. PATENT DOCUMENTS

| | | | |
|---|---|---|---|
| 2,772,237 | 11/1956 | Bauman et al. | 568/872 X |
| 3,315,002 | 4/1967 | Small | 568/872 |
| 3,507,891 | 4/1970 | Hearne et al. | 260/410.9 R |
| 3,880,939 | 4/1975 | Corn et al. | 568/872 X |
| 3,906,016 | 9/1975 | Isa et al. | 260/410.9 R |
| 4,041,057 | 8/1977 | Fanning | 260/410.9 R |
| 4,168,390 | 9/1979 | Alfs et al. | 568/793 |

Primary Examiner—Helen M. S. Sneed
Attorney, Agent, or Firm—Wells & Wells

[57] ABSTRACT

A method for preparing carboxylic acid alkylester after products free of nitrogen containing compounds. These after products, free of nitrogen containing compounds, are prepared by:

(1) reacting olefins with carbon monoxide and alkanols in the presence of a catalyst system consisting of a cobalt compound and pyridine, non-orthosubstituted alkylpyridines or a mixture of these pyridines at elevated pressures and elevated temperatures to produce carboxylic acid alkylesters containing nitrogenated compounds resulting from the pyridines;

(2) hydrogenating the carboxylic acid alkylesters to produce after products which include alcohols; and (3) treating the after products with acid ion exchangers to remove the nitrogenated compounds.

6 Claims, No Drawings

PROCESS FOR PRODUCING CARBOXYLIC ACID ALKYLESTER AFTER PRODUCTS EXTENSIVELY FREE FROM NITROGENATED COMPOUNDS

CROSS-REFERENCE TO RELATED APPLICATIONS

Applicants claim priority under 35 USC 119 for application P 30 46 651.4, filed Dec. 11, 1980 in the Patent Office of the Federal Republic of Germany.

The disclosure of coinventor Hofmann's copending application, Ser. No. 125,482, filed Feb. 28, 1980 is incorporated herein to show alkoxycarbonylation procedures carried out in the presence of cobalt catalysts and a promoter from the group pyridine, non-ortho-substituted alkylpyridine and mixtures thereof.

Also incorporated herein is coinventor Hofmann's copending application Ser. No. 203,393, filed Nov. 3, 1980 to show that olefins with internal double bonds can be produced by dehydrogenation of paraffins or by chlorination followed by dehydrochlorination of paraffins.

BACKGROUND OF THE INVENTION

The field of the invention is the hydrogenation of alkyl esters of saturated aliphatic carboxylic acids and the present invention is particularly concerned with reacting olefins with carbon monoxide and alkanol in the presence of a catalyst consisting of a cobalt compound and a promoter selected from pyridine, non-ortho-substituted alkylpyridine or mixtures thereof at elevated pressures and elevated temperatures, hydrogenating the esters produced and treating them with an acid ion exchanger.

The state of the art of such alkoxycarbonylation reactions may be ascertained by reference to U.S. Pat. Nos. 3,507,891; 3,906,016 and 4,041,057 and the article "Hydrocarboxymethylation—an Attractive Route from Olefins to Fatty Acid esters?" by Peter Hofmann et al as published in I & EC, Product Research & Development, Vol. 19, Sept. 1980, pp. 330–334, the disclosures of which are incorporated herein.

The state of the art of hydrogenation of esters may be ascertained by reference to the Kirk-Othmer, "Encyclopedia of Chemical Technology", vol. 8 (1966), pages 365–382, under the section entitled, "Esters, Organic", particularly pages 369–370 and F. Zymalkowsky's "Katalytische Hydrierungen", published by F. Enke, Stuttgart, Germany (1965).

Acid ion exchange resins useful in the present invention are disclosed in U.S. Pat. No. 4,168,390 and "Ullmanns Enzyklopaedie der Technischen Chemie", Chemie GmbH publishers, Weinheim/Bergstr., Germany (1977), 4th ed., vol. 13, pp. 279–346, "Ion Exchangers".

Examples of these acid ion exchange resins are LEWATIT (R) products manufactured by Bayer AG Leverkusen, West Germany, designated
  LEWATIT SPC 108 H
  LEWATIT SPC 118
  LEWATIT SC 102 H
  LEWATIT SC 104 H
  LEWATIT SC 108 H
  LEWATIT CNP 80

It is known that by reacting olefins with carbon monoxide and a compound having a replaceable hydrogen atom such as an alkanol in the presence of a catalyst containing a metal of Group VIII of the Periodic Table of elements and possibly a promotor, fatty acid esters can be produced as disclosed in J. Falbe, Synthesen mit Kohlenmonoxid, Springer publishers, Berlin, Heidelberg, New York (1967).

An especially preferred variation of this reaction, which is termed alkoxycarbonylation, is the conversion in the presence of cobalt catalysts. The rate, the selectivity and the yield in linear fatty acid esters of the cobalt reaction can be increased by adding promoters belonging to the pyridine class of compounds. Pyridine itself and also non-ortho-substituted alkylpyridines and mixtures thereof have been found particularly effective.

The carboxylic acid esters obtained by alkoxycarbonylation are products with many applications. These esters may be further processed into alcohols, for instance, among other substances. The alcohols made according to this process, because of the use of nitrogen-containing promoters (pyridine and/or non-orthosubstituted alkylpyridines) in the alkoxycarbonylation stage, are contaminated by slight amounts of nitrogen-containing compounds. Commercially produced alcohols, made for instance by hydroformylation, Ziegler synthesis reaction, paraffin oxidations or by fat splitting, as a rule do not contain such contaminants. It is appropriate therefore to prepare the products which are sequential to the carboxylic acid alkylesters obtained by alkoxycarbonylation, preferably alcohols, in such a manner that they are free or extensively free of nitrogen-containing compounds.

It is not possible to sufficiently eliminate the nitrogen-containing compounds by distilling the alcohols or the carboxylic acid esters used as the previous stage. Even when distillation columns with a higher number of trays or plates are used and high reflux ratios are observed, no more than a rather uniform distribution of the nitrogen compounds into all the distillate fractions is obtained.

Even when the alcohols or the carboxylic acid esters are treated with adsorbents, such as activated carbon, aluminum oxide of various activities or silica, no more than an inadequate elimination of the nitrogen contaminations can be achieved.

Lastly, the nitrogen contaminations can be only insufficiently removed if the carboxylic acid esters are treated with acid ion exchangers prior to hydrogenation.

SUMMARY OF THE INVENTION

Having in mind the limitations of the prior art, it is an object of the present invention to create a commercial and technically simple process for the production of after-products substantially rid of nitrogen-containing compounds, preferably these products being alcohols, and having been prepared from alkoxycarbonylated carboxylic acid alkylesters.

According to the present invention: (1) carboxylic acid alkylesters are produced by reacting olefins with carbon monoxide and alkanols in the presence of a catalytic system consisting of a cobalt compound and pyridine and/or a non-orthosubstituted alkylpyridine at elevated pressures and elevated temperatures; (2) the carboxylic acid alkylesters containing nitrogen compounds resulting from the pyridines are hydrogenated to after product alcohols; and (3) the after product alcohols are treated with an acid ion exchanger to remove the nitrogen compounds.

By elevated temperatures is meant about 80° to 300° C., preferably 150° to 200° C. By elevated pressures is meant carbon monoxide pressures of about 10 to 800, preferably 100 to 300 bars.

DESCRIPTION OF THE PREFERRED EMBODIMENTS

It was new and unexpected that the nitrogen-containing compounds from the promoter should be convertible under the typically mild conditions applying to ester hydrogenation into a form allowing complete or extensive removal by an ensuing treatment by an acid ion exchanger as disclosed by F. Zymalkowsky, ibid., Chap. XI, p. 118.

On the other hand it was unexpected that the effectiveness of the catalyst used for the ester hydrogenation is not degraded in spite of the presence of the nitrogen-containing compounds usually considered catalyst-poisons as disclosed by F. Zymalkowsky, ibid., Chap. IV, p. 34 and Organic Reactions, John Wiley & Sons, New York (1954), vol. VIII, page 11.

The carboxylic acid alkylesters used in the process of the present invention can be obtained by any alkoxycarbonylation reaction wherein olefins are reacted with carbon monoxide and alkanols in the presence of a catalytic system consisting of a cobalt compound and pyridine and/or a non-ortho-substituted alkylpyridine at elevated pressures and elevated temperatures, as disclosed in U.S. patent application Ser. No. 125,482 and U.S. Pat. No. 3,507,891. The selection of the olefin used is not critical, that is, both straight-chain or branched alpha-olefins and olefins with internal double bonds are useful. However, olefins with more than one double bond and those with substituents, for instance, aryl-, carboximethyl- and hydroxyl-groups are also suitable.

As a rule olefins having 2 to 40, preferably 4 to 20 C atoms are used. For example, alpha-olefins are prepared by the Ziegler ethylene synthesis reaction or by wax-cracking. Olefins with internal double bonds, which are preferred for the process of the present invention, are prepared by catalytically dehydrogenating paraffins or by chlorinating paraffins and then dechlorinating the chloro-paraffins as disclosed in U.S. patent application Ser. No. 203,393.

In the method disclosed in U.S. patent application Ser. No. 203,393, paraffin blends, that is, mixtures with different C numbers are used as a rule, whereby the olefins obtained lack a uniform C number. Moreover, all conceivable isomeric forms are obviously present in these olefin mixtures.

Besides that pure and possibly substituted olefins, olefins are also used which contain paraffins for instance up to 85% by weight. There is a content of paraffin because conversion is not complete in the olefin production, and the unconverted paraffins are not separated, or are only incompletely separated.

Not only the input olefin, but also the kind of alkanol being reacted with the olefin and the carbon monoxide is not critical for the carboxylic acid alkylesters used in the process of the present invention. As a rule, alkanols having 1 to 10, preferably 1 to 4 C atoms are used. Typical representative substances of the primary alcohol groups are, for instance, methanol, ethanol, propanol-(1) and butanol-(1).

Again, it is not essential which cobalt compound is used in the alkoxycarbonylation. Cobalt carbonyls, for instance, dicobaltoctacarbonyl, are just as suitable as carboxylic acid cobalt salts such as cobalt acetate, cobalt naphthenate and cobalt-2-ethylhexanoate and salts of cobalt with inorganic acids such as cobalt nitrate and cobalt sulfate. Preferably, carboxylic acid cobalt salts are used where the anions correspond to the acid group of the fatty acid esters formed in the alkoxycarbonylation.

Applicable promoters are pyridine and all non-orthosubstituted alkylpyridines such as 3-picoline and 4-picoline, 3,4- and 3,5-lutidine and 3-ethylpyridine and 4-ethylpyridine, or mixtures of these pyridines.

Lastly, the conditions of reaction under which the alkoxycarbonylation is carried out are not significant. As a rule, the alkoxycarbonylation processes are carried out at temperatures of about 80° to 300°, preferably 150° to 220° C., and at carbon monoxide pressures of about 10 to 800, preferably 10 to 300 bars. Depending on the kind of olefin being converted, the concentration of the cobalt used as the catalyst is in a range from about 0.005 to 0.2 gram-atom of cobalt per mole of olefin and the amount of the pyridine and/or non-orthosubstituted alkylpyridine being used as a co-catalyst is in a range from about 3 to 100, preferably 5 to 50 moles per gram-atom of cobalt. The amount of the alkanol used per mole of olefin is in a range from about 1 to 20, preferably 1 to 10 moles.

What is critical for the process of the present invention, however, is the kind and the sequence of the individual process steps which permit the preparation of after-products, widely rid of nitrogen compounds, from the carboxylic acid alkyl esters obtained by alkoxycarbonylation. Within the scope of the present invention, the term after-products applies predominantly to the alcohols obtained by hydrogenating the carboxylic acid alkylesters, which correspond in their C numbers to the carboxylic acids basic to the esters. Also, furthermore, the term after-product is applied to all compounds which may be obtained from these alcohols by further reactions. Such compounds, for instance, are aldehydes, carboxylic acids, oxethylates, sulfates and ethersulfates.

In general, the procedure of the process of the present invention is such that the carboxylic acid alkylesters which are rid as much as possible from the remaining substances of the alkoxycarbonylation mixture are first hydrogenated. This hydrogenation is carried out under conditions typical for the ester and using a catalyst, preferably a copper-chromite catalyst. Typical conditions for an ester hydrogenation are temperatures from about 150° to 230°, preferably 180° to 200° C. and pressures of 200 to 400, preferably 250 to 350 bars of hydrogen. More definitive details of the hydrogenation are found in the pertinent literature, for instance, in F. Zymalkowsky's Katalytische Hydrierungen, F. Enke publishers, Stuttgart 1965.

Following hydrogenation, the alcohol, which corresponds in its C number to the carboxylic acid basic to the carboxylic acid alkylester, is treated by means of an acid ion exchanger. Preferably the treatment is carried out in the presence of the alcohol corresponding to the alkyl component of the carboxylic acid alkylester. As a rule, this alcohol is present in an amount which corresponds to the stoichiometric composition of the carboxylic acid alkylester used for hydrogenation. The alcohol, if appropriate, can be separated subsequently by separation methods such as distillation or rectification. Suitable acid ion exchangers for the process of the present invention are preferably styrene-divinylbenzene copolymers bearing sulfonic acid groups and copolymers of acrylic acid or acrylic-acid derivatives and divinylbenzene bearing carboxyl groups as disclosed in Ullmanns, ibid.

The treatment with an acid ion exchanger is carried out, for instance, in a so-called exchanger column at standard conditions (20° C., 1 bar). Obviously, deviations from the kind and conditions of treatment are possible to the extent they are appropriate or are required by the physical properties of the substance to be purified.

Using the process of the present invention, it is possible to prepare after-products of carboxylic acid alkylesters obtained by alkoxycarbonylation wherein the content in nitrogen compounds stated as elementary nitrogen is less than 20, preferably less than 1 ppm by weight.

The examples below further explain the process of the invention.

CONTROL EXAMPLE A

A raw product obtained by reacting a statistical isomeric mixture of n-undecenes, n-dodecenes and n-tridecenes under the conditions described in Example 1 of U.S. patent application Ser. No. 125,482 was subjected to rectification to obtain a product consisting mainly of the methylesters of the carboxylic acids which were enriched by one carbon atom over the input olefins. Nitrogen-containing compounds remained in the ester mixture obtained after rectification, where the nitrogen-containing compounds were no gamma-picoline, and which was determined to have an analytically ascertained nitrogen content of 147 ppm. After hydrogenating the esters using a copper-chromite catalyst at 300 atm and 210° C., the primary alcohols which were predominantly generated during the hydrogenation evinced a nitrogen content of 145 ppm. The fractions obtained in an ensuing discontinuous rectification in a packed column with about 30 theoretical separation stages and for a reflux ratio of 5 contained between 32 and 1.450 ppm of nitrogen. The fractions containing $C_{12}$- to $C_{14}$-alcohols on the average contained 118 ppm of nitrogen.

CONTROL EXAMPLE B

The reprocessing of the ester mixture of control example A was carried out in such a manner than the ester mixture is first made to pass over a commercial ion exchanger (LEWATIT® SPC 118, Bayer AG) at 25° C. before being hydrogenated using a copper-chromite catalyst. The nitrogen content after the ion-exchanger treatment amounted to 91 ppm, 90 ppm after the hydrogenation and on the average 75 ppm after the rectification in the fractions containing the $C_{12}$- to $C_{14}$-alcohols.

EXAMPLE 1

The ester mixture of the control example A was treated at 25° C. with a commercial ion exchanger (LEWATIT® SPC 118, Bayer AG) under the conditions stated in control example B but not before hydrogenation, rather after it. The nitrogen content of 147 ppm in the ester mixture and of 145 ppm in the hydrogenaation product of comparative example A thereby was lowered to less than 1 ppm. The average nitrogen content in the $C_{12}$- to $C_{14}$-alcohol fractions also was less than 1 ppm.

EXAMPLE 2

Example 1 was repeated except that in lieu of the commercial ion exchanger LEWATIT® SPC 118, the commercial ion exchanger LEWATIT® CNP 80 (also by Bayer AG) was used. The average nitrogen content in the $C_{12}$- to $C_{14}$-alcohol fractions was 2 ppm.

We claim:

1. In a method for preparing carboxylic acid alkylester after products comprising:
    (a) reacting olefins with carbon monoxide and alkanols in the presence of a catalyst system consisting essentially of a cobalt compound and a promoter selected from the group consisting of pyridine, non-orthosubstituted alkylpyridines or mixtures thereof at elevated temperatures and elevated pressures to produce carboxylic acid alkylesters having compounds containing nitrogen resulting from said promoter; and
    (b) hydrogenating said carboxylic acid alkylesters to produce after products which include alcohols;
    the improvement comprising freeing said after products of said compounds containing nitrogen by:
    (c) hydrogenating said compounds containing nitrogen simultaneously with said carboxylic acid alkylesters; and
    (d) separating said hydrogenated compounds containing nitrogen from said after products with acid ion exchangers.

2. The method of claim 1, wherein said elevated temperatures are about 80° to 300° C. and said elevated pressures are about 10 to 800 bars.

3. The method of claim 2, wherein said after products include an alcohol corresponding in its C number to that of a carboxylic acid produced in step (a).

4. The method of claim 2, wherein said hydrogenation is carried out at temperatures of about 150° to 230° C. and at pressures of about 200 to 400 bars while using a copper-chromite catalyst.

5. The method of claim 4, wherein said acid ion exchanger is selected from the group consisting of a sulfonated styrene-divinylbenzene copolymer, a carboxyl-group containing a copolymer of acrylic acid and a carboxyl-group containing a copolymer of a derivative of acrylic acid and divinylbenzene.

6. The method of claim 5, wherein step (c) is carried out in the presence of an alkanol which corresponds to the alkyl component obtained in step (a).

* * * * *